United States Patent
Feng et al.

(10) Patent No.: US 7,593,110 B2
(45) Date of Patent: Sep. 22, 2009

(54) SURFACE PLASMON RESONANCE DETECTING APPARATUS AND METHOD THEREOF

(75) Inventors: Chih-Cheng Feng, Taipei (TW); Hsueh-Ching Shih, Taipei County (TW); Ting-Hsuan Chen, Taipei (TW)

(73) Assignee: Industrial Technology Research Institute, Hsinchu (TW)

(*) Notice: Subject to any disclaimer, the term of this patent is extended or adjusted under 35 U.S.C. 154(b) by 157 days.

(21) Appl. No.: 11/937,506

(22) Filed: Nov. 9, 2007

(65) Prior Publication Data

US 2009/0097032 A1    Apr. 16, 2009

(30) Foreign Application Priority Data

Oct. 12, 2007    (TW) .............................. 96138172 A

(51) Int. Cl.
*G01N 27/30* (2006.01)
(52) U.S. Cl. ..................................... 356/445
(58) Field of Classification Search ......... 356/445–448, 356/436–444; 422/82.05, 55–58
See application file for complete search history.

(56) References Cited

U.S. PATENT DOCUMENTS

| | | | |
|---|---|---|---|
| 6,384,953 B1* | 5/2002 | Russell et al. ............... | 359/245 |
| 6,982,819 B2* | 1/2006 | Sawin et al. ................. | 359/245 |
| 7,474,404 B2* | 1/2009 | VanWiggeren ............... | 356/445 |
| 2002/0171841 A1* | 11/2002 | Elkind et al. ................. | 356/445 |
| 2004/0090631 A1* | 5/2004 | Elkind et al. ................. | 356/445 |
| 2005/0117158 A1* | 6/2005 | Kanai et al. .................. | 356/445 |
| 2008/0163688 A1* | 7/2008 | Wang et al. ................... | 73/580 |
| 2008/0198384 A1* | 8/2008 | Ran et al. ..................... | 356/445 |
| 2008/0285033 A1* | 11/2008 | Wang et al. .................. | 356/364 |

FOREIGN PATENT DOCUMENTS

| TW | I249768 | 2/2006 |
|---|---|---|
| TW | I262309 | 9/2006 |
| TW | 200724906 | 7/2007 |

* cited by examiner

*Primary Examiner*—Hoa Q Pham
(74) *Attorney, Agent, or Firm*—Jianq Chyun IP Office

(57) ABSTRACT

A surface plasmon resonance (SPR) detecting apparatus which controls the flow of fluid without using an additional pressure difference or pump is provided. The SPR detecting apparatus includes a detection chip, a fluid driving chip and an optical device. The fluid driving chip has a plurality of electrodes disposed on the flow space of the fluid. The angle between the liquid and a contact surface is changed by electrifying the electrodes, and the electrodes are turned on and turned off sequentially such that the droplets are controlled to move. The optical device is used to detect surface plasmon resonance phenomenon and to determine the interaction of the droplets and the detecting chip.

25 Claims, 3 Drawing Sheets

SURFACE PLASMON RESONANCE DETECTING APPARATUS AND METHOD THEREOF

CROSS-REFERENCE TO RELATED APPLICATION

This application claims the priority benefit of Taiwan application serial no. 96138172, filed on Oct. 12, 2007. The entirety of the above-mentioned patent application is hereby incorporated by reference herein and made a part of this specification.

BACKGROUND OF THE INVENTION

The present invention relates to a surface plasmon resonance (SPR) detecting apparatus and a method thereof, and more particularly, to an SPR detecting apparatus using an electrode induction electrowetting method.

At present, fluids required by biochemical detection chips are all continuous fluid, and most common driving technology of biochemical detection chips use a pressure difference and a tubing pump to provide a necessary driving force. However, due to the requirements of miniaturization and precision on the detection technology, the usage of continuous fluid will suffer the following problems. For example, a cross-infection between detection chip and a sample, a block in a pipeline of a micro-channel, and residual in the channel will influence the result of next detection. Moreover, if a continuous fluid is used, a great amount of sample is demanded as a sample solution must fill up the whole channel from a driving force source to the detection chip. Therefore, the biochemical detection chip is hard to be applicable for a small amount of sample and will waste a lot of valuable samples. In addition, the pump for driving the continuous fluid has a large volume and is hard to be integrated into a system.

At present, a fluid in a common biochemical detection system is usually conveyed in a continuous manner. For example, a driving device (such as a pump) is used to push liquid to continuously flow into a fluid passageway (such as a pipeline and a channel). If the width of the channel is 1 cm or more, a mechanical precision processing method may be adopted to manufacture the channel; and if the width of the channel is smaller than 1 cm, a simple micro-channel manufacturing technology is adopted to manufacture the channel. For example, with regard to a fluid transfer system manufactured by an SPR manufacturer Biacore Company, in U.S. Pat. No. 6,008,893, a fluid is driven by a tubing pump to flow into a testing area through a pipeline, and a reaction signal is detected by an optical system in the testing area. In another U.S. Pat. No. 6,698,454 of Biacore Company, a mechanical precision processing method is adopted to manufacture a channel, and a fluid under test is driven by an external pump. In U.S. Pat. No. 7,193,703 of Fuji Photo Film Co., Ltd., the mechanically processed channel of an SPR detecting apparatus penetrates into a prismatic structure, and after a liquid under test flows into the channel, a light is irradiated on a detection area to perform the detection.

The aforementioned patents are all developed to control the continuous fluid. However, the innovative idea of controlling discrete droplets may in a more advanced manner. In aspect of technology, some documents about an electrowetting method for controlling a fluid have been published in recent years, but such a method have not been applied in an apparatus integrated with a biochemical detection system.

SUMMARY OF THE INVENTION

In view of the above, the present invention is directed to provide an SPR detecting apparatus and a method thereof. A detection chip and a fluid driving chip are integrated to form an architecture enabling a detection system to accurately control the liquid amount of a discontinuous fluid to detect a biochemical reaction, programmable procedures as user defined, enhance detection efficiency, and simplify the system architecture.

The present invention is further directed to provide an SPR detecting apparatus and a method thereof, which utilize the electrowetting technology to improve the conventional technology of driving a sample by means of an external pump or pressure difference, so as to solve the problems such as a detection chip and a sample are cross-infected, a pipeline of a micro-channel is blocked, the channel has residual, and the sample solution is wasted.

The present invention provides an SPR detecting apparatus, which includes a detection chip and a fluid driving chip. The detection chip has a metal film thereon, which has a SPR characteristic and has at least one detection area. The fluid driving chip has a droplet control device, which includes at least one first electrode and at least one second electrode, and the first electrode is separated from the second electrode. A space for a droplet to pass through is formed between the metal film and the fluid driving chip. A relative voltage is provided between the first electrode and the second electrode to drive the droplets in the space.

The present invention provides an SPR detecting method, which includes first providing an SPR detecting apparatus. The SPR detecting apparatus includes a detection chip, a fluid driving chip, and an optical device. The detection chip has a metal film thereon, which has a SPR characteristic and has a plurality of detection areas. The fluid driving chip has a droplet control device, which includes a plurality of first electrodes and a plurality of second electrodes disposed at different positions in an insulation layer. A space for a droplet to pass through is formed between the metal film and the insulation layer. The optical device is disposed on the detection chip, and includes a light source and a detector. Then, at least one droplet is supplied to the space between the metal film and the insulation layer. A relative voltage is provided between the first electrodes and the second electrodes, so as to generate a driving force to drive the droplet to a detection position. Light from the light source is incident on the metal film, so as to generate a surface plasmon resonance wave on the metal film, and generate a reflected light at the same time. At this time, the detector detects the status of the reflected light.

In order to make the aforementioned and other objects, features and advantages of the present invention comprehensible, preferred embodiments accompanied with figures are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Surface plasmons, also known as surface plasmon polaritons, are surface electromagnetic waves that propagate parallel along a metal/dielectric interface. Since the wave is on the boundary of the metal and the external medium, these oscillations are very sensitive to any change of this boundary, such as the adsorption of molecules to the metal surface. That is why this technique broadly used in biochemical experiments. When a light beam penetrates a glass medium to reach a junction interface of the glass and a metal film, an optical physical phenomenon will be generated along with the total internal reflection. The incident light beam will be totally reflected when reaching an interface of the glass and air in a propagation conduction path. However, in fact, a part of light energy is transmitted on the surface of the metal film in form of an evanescent wave.

When the incident light is coupled via a prism to increase the wave vector thereof, and is guided by a medium, the incident light in transverse mode (TM) is coupled with free electron charges on the surface, thereby generating surface plasmon waves. Generally, the material of the metal film is preferably gold (Au) or silver (Ag), but metals such as copper, titanium, or chromium can also support surface plasmon generation.

Therefore, when the incident light and metal atoms in the metal film resonate, the reflection strength may be changed dramatically in a specific range of reflection angle. Such a reflection angle is also referred to as a resonance angle, which is changed as the refraction coefficient of the medium adjacent to the metal film.

Figure 1:
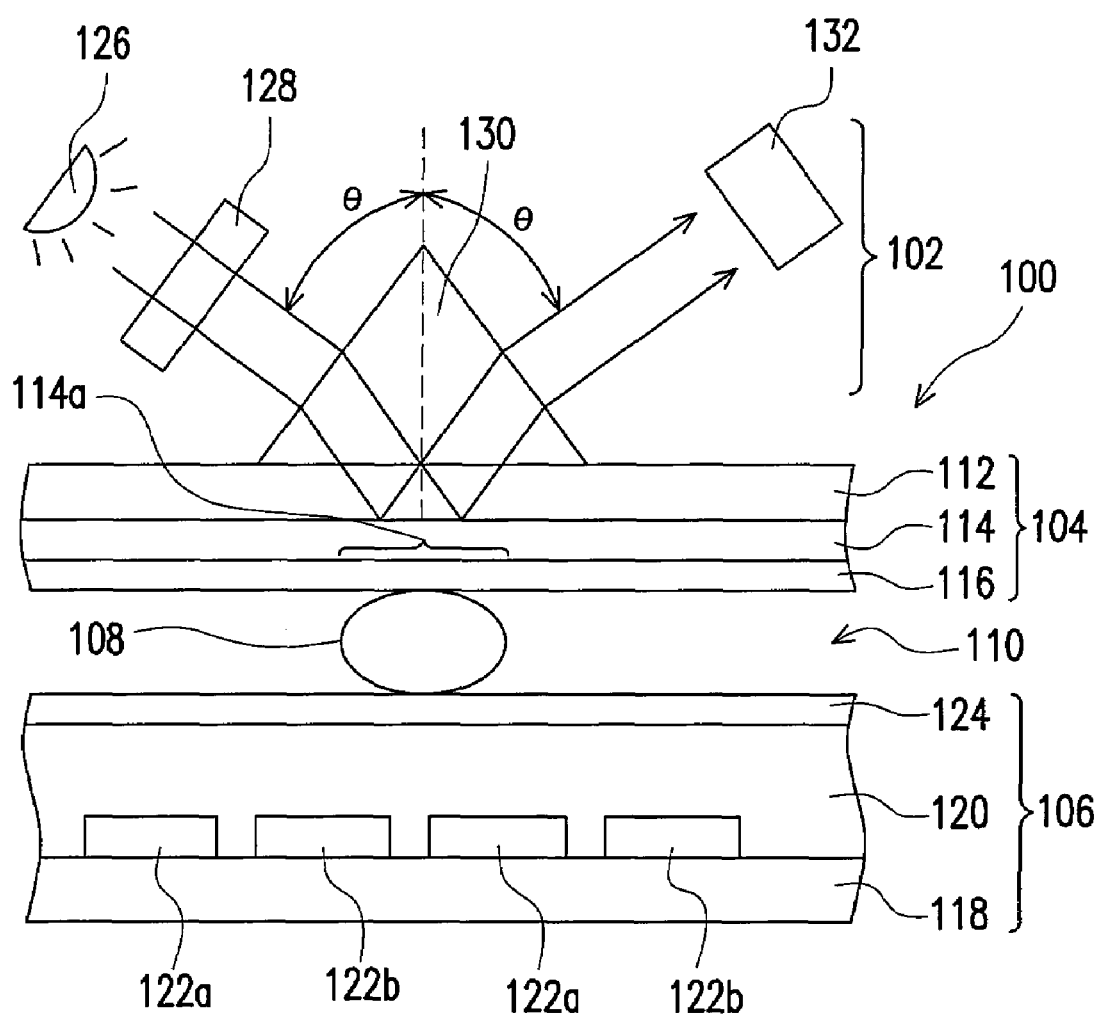
FIG. 1 is a schematic view of the SPR detecting apparatus according to an embodiment of the present invention.
Figure 2:
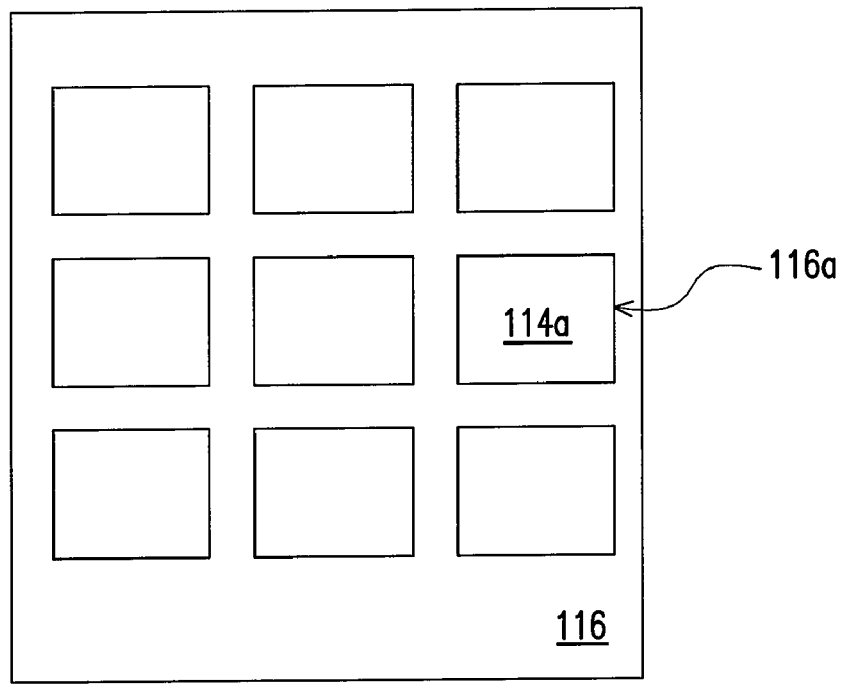
FIG. 2 is a schematic view of the detection chip according to an embodiment of the present invention.
Figure 3:
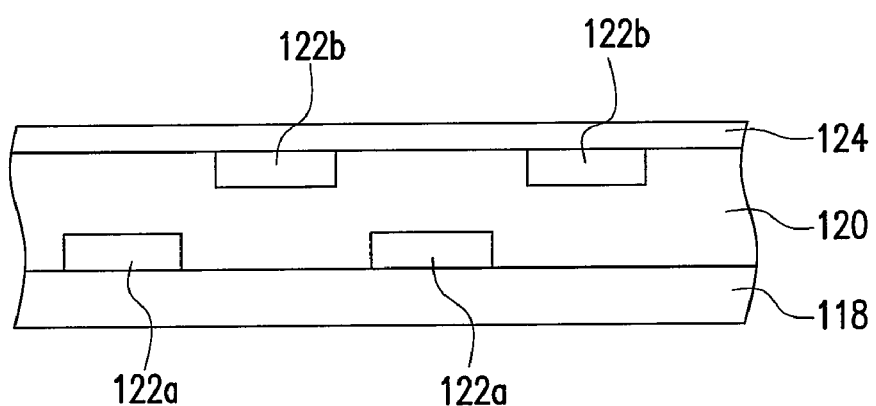
FIG. 3 is a schematic view of the fluid driving chip according to another embodiment of the present invention.
Figure 4:
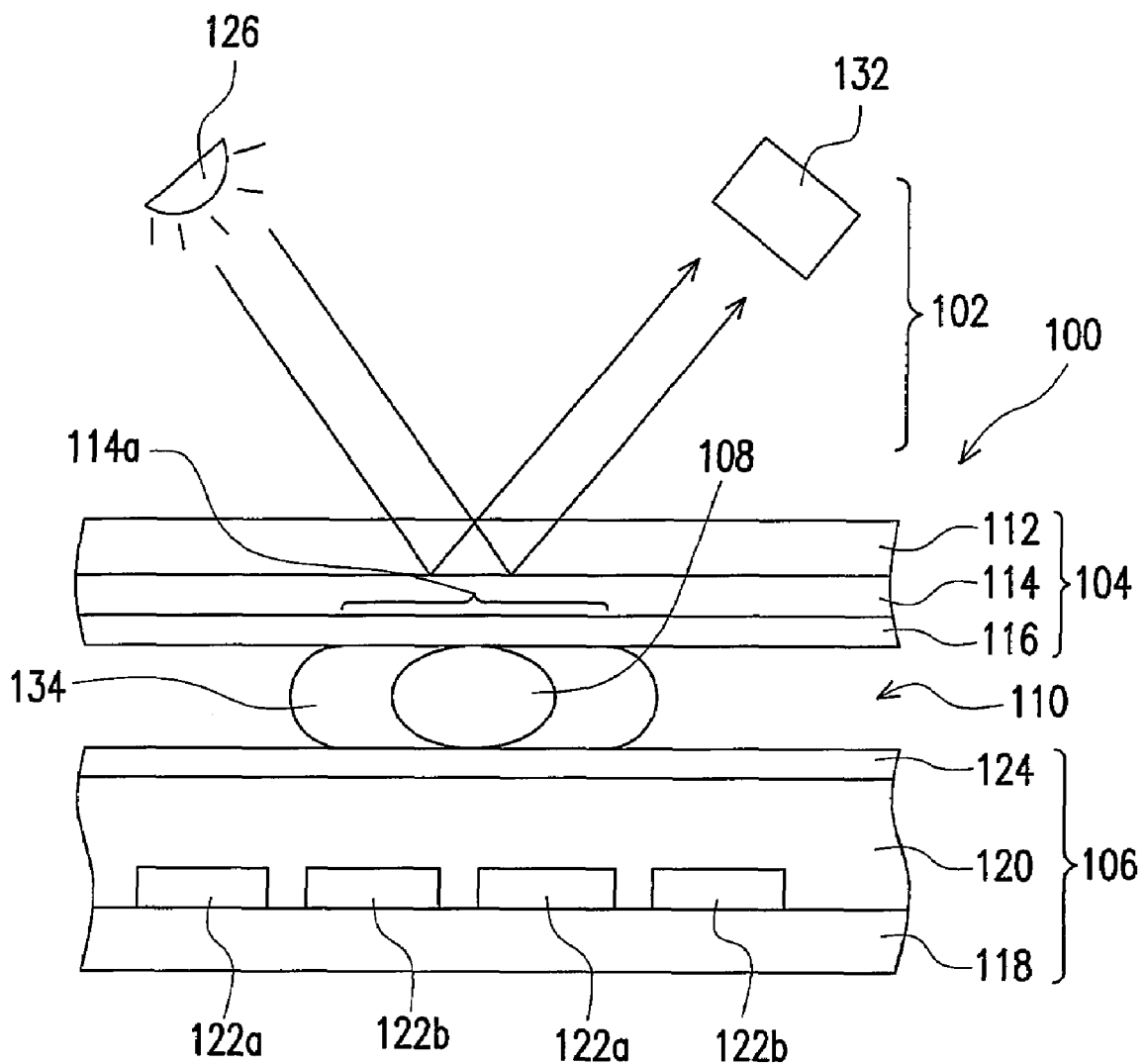
FIG. 4 is a schematic view of the SPR detecting apparatus according to another embodiment of the present invention.

FIG. 1 is a schematic view of the SPR detecting apparatus according to an embodiment of the present invention. FIG. 2 is a schematic view of the detection chip according to an embodiment of the present invention. FIG. 3 is a schematic view of the fluid driving chip according to another embodiment of the present invention. FIG. 4 is a schematic view of the SPR detecting apparatus according to another embodiment of the present invention.

As shown in FIG. 1, the SPR detecting apparatus 100 includes an optical device 102, a detection chip 104, and a fluid driving chip 106. The optical device 102 is, for example, disposed on the detection chip 104. A clearance is saved between the detection chip 104 and the fluid driving chip 106 as a space 110 for a droplet 108 to pass through.

The detection chip 104 includes a transparent substrate 112, a metal film 114, and a hydrophobic layer 116. The transparent substrate 112 is disposed on the metal film 114 and between the metal film 114 and the optical device 102. The material of the transparent substrate 112 is, for example, glass, and definitely may be other transparent materials.

The material of the metal film 114 includes a metal material which may generate SPR, such as gold, silver, copper, titanium, chromium and the mixture thereof. The metal film 114 may have a detection area 114a. Light from the optical device 102 (i.e., a light source) is incident on the metal film 114 to generate a surface plasmon resonance wave, and may also be incident on the detection area 114a. In the detection area 114a, the metal film 114 is influenced by the droplet 108 to change the SPR characteristic thereof. That is to say, compared with the metal film not contacting with a droplet, the metal film (the detection area) contacting with the droplet has the SPR characteristic changed, and thus the droplet may be detected. A specific biological antibody or a substance which will combine or disassociate with the components in the droplet may also be grown on the metal film 114 upon actual situation.

The hydrophobic layer 116 is, for example, disposed on the metal film 114. The hydrophobic layer 116 may have at least one opening 116a optionally to expose the detection area 114a (as shown in FIG. 2) of the metal film 114. The material of the hydrophobic layer 116 includes polytetrafluoroethylene or perfluoropolymer.

The fluid driving chip 106 includes a droplet control device. The droplet control device includes a substrate 118, an insulation layer 120, a plurality of first electrodes 122a, a plurality of second electrodes 122b, and a hydrophobic layer 124.

The material of the substrate 118 includes glass. The insulation layer 120 is, for example, disposed on the substrate 118. The material of the insulation layer 120 includes $SiO_2$, $Si_3O_4$, $S_fO_xN_y$, strontium barium titanate (BST), polymer, photoresist SU-8, or Parylene. The insulation layer 120 prevents the droplet from directly contacting with the first electrodes 122a or the second electrodes 122b.

The plurality of first electrodes 122a and the plurality of second electrodes 122b are disposed at different positions in the insulation layer 120, and the plurality of first electrodes 122a and the plurality of second electrodes 122b are separated from one another. For example, the plurality of first electrodes 122a and the plurality of second electrodes 122b are arranged and disposed in and offset manner. Of course, only one first electrode 122a or second electrode 122b may also be disposed.

Furthermore, as shown in FIG. 1, the plurality of first electrodes 122a and the plurality of second electrodes 122b abut against the substrate 118 (a lower surface of the insulation layer 120), i.e., the first electrodes 122a and the second electrodes 122b are disposed at the same side of the insulation layer 120. Alternatively, as shown in FIG. 3, the first electrodes 122a abut against the lower surface (the substrate 118) of the insulation layer 120, and the second electrodes 122b abut against an upper surface of the insulation layer 120, i.e., the first electrodes 122a and the second electrodes 122b are disposed above and below the insulation layer 120, respectively. The orthographic projection planes of the plurality of first electrodes 122a and the plurality of second electrodes 122b are not overlapped with each other. The material of the plurality of first electrodes 122a and the plurality of second electrode 122b includes metal, for example, Ti, ITO, Al, Cu, or Au. The plurality of first electrodes 122a and the plurality of second electrodes 122b are formed after, for example, an electrode material is formed on the substrate 118, and then exposed, developed, and etched through a micro-electro-mechanical process, so as to be patterned. The shape of the electrode is allowed as long as it may provide a sufficient force to drive the droplets, so it is not limited.

The hydrophobic layer 124 is, for example, disposed on the insulation layer 120. The material of the hydrophobic layer 124 includes polytetrafluoroethylene or perfluoropolymer. The hydrophobic layer 124 and the hydrophobic layer 116 are opposite to each other, i.e., the hydrophobic layer 116 is disposed outside the metal film 114. The hydrophobic layer 124 is disposed between the hydrophobic layer 116 and the insulation layer 120.

The space 110 for the droplet 108 to pass through is formed between the metal film 114 and the insulation layer 120, and by providing a relative voltage between the plurality of first electrodes 122a and the plurality of second electrodes 122b, the droplet is driven in the space 110 to move to the detection area 114a.

The optical device 102 is disposed on the detection chip 104, and includes a light source 126 and a detector 132, and may be disposed with a polarizer 128 and a prism 130 optionally.

The light source 126 is disposed on the detection chip 104. The polarizer 128 is disposed between the light source 126 and the prism 130. The prism 130 is disposed between the light source 126 and the detector 132. The light from the light source 126 passes through the polarizer 128, the prism 130, and then is incident on the detection area 114a to generate a surface plasmon resonance wave. The reflected light passes through the prism 130 and is incident on the detector 132. In the detection area 114a, the metal film 114 contacts with the droplet 108, the status of the surface plasmon resonance wave is changed, and then the status of the reflected light is changed. The reflected light passes through the prism 130 to be incident on the detector 132. The detector 132 is used to detect the status of the reflected light.

The aforementioned SPR detecting apparatus mainly includes the optical device 102, the detection chip 104, and the fluid driving chip 106. The fluid driving chip 106 is disposed below the detection chip 104, and a specific space is saved between the detection chip 104 and the fluid driving chip 106 to guide the droplet 108 into the detection area.

In the detection chip 104, a transparent substrate (such as glass) is used to be coated with a metal film, such that the metal film 114 generates SPR. Furthermore, in order to reduce the friction force between the droplets 108 and the fluid driving chip 106 and/or the metal film 114 for convenient control, the films (such as the hydrophobic layers 116 and 124) made of a hydrophobic material are coated on the fluid driving chip 106 and/or the metal film 114. It should be noted that the hydrophobic films cannot be too thick to influence the detection of a device on an SPR signal. In addition, if the droplet 108 is a biologic sample, which should contact with the metal film 114 directly, in the detection area 114a, the hydrophobic layer 116 should be removed for reaction.

In order to form the first electrode 122a and the second electrode 122b (positive and negative poles) on the substrate 118, in the fluid driving chip 106, an insulation layer is coated above the electrodes (i.e., the first electrode 122a and the second electrode 122b), so as to prevent the droplet from directly contacting with the electrodes (i.e., the first electrode 122a and the second electrode 122b). According to the hydrophilic and hydrophobic characteristics of the surface of the insulation layer on the top portion, it should be determined whether to coat a hydrophobic layer 124. The fluid driving chip 106 provides a droplet driving force by using an electrowetting method. When a voltage is applied on the two electrodes (i.e., the first electrode 122a and the second electrode 122b), the two electrodes (the first electrode 122a and the second electrode 122b) generates an induced electric field due to a potential difference. The induced electric field penetrates an equivalent capacitance caused by the insulation layer to enter the droplet and generates induced charges within the droplet 108, thereby changing the energy state on the surface of the droplet 108 and change the contact angle between the liquid and solid. When the contact angles on the two sides of the droplet 108 are not equal, the force imbalance occurs to cause movement of the droplet. Therefore, the droplet 108 tends to stay at a place where the electrified fields are dense, so as to achieve the balance. The movement of the droplet may be controlled by switching the electrode pairs sequentially, and after that, the droplet 108 may move according to the switching sequence. The applied voltage should not cause the insulation layer to break down.

The optical device 102 includes the light source 126, the polarizer 128, the prism 130, and the detector 132. For example, SPR may be detected by means of intensity interrogation, wavelength interrogation, phase interrogation, and etc. The light (which may be 780 nm) from the light source 126 passes through the polarizer 128 to adjust a polarizing angle to be a transverse mode (TM) wave, then is incident on the prism 130, and reflected by the surface of the metal film, so as to make the incident angle be equal to the reflection angle and generate a surface plasmon resonance wave on the surface of the metal film. Subsequently, the detector 132 is used to detect the status of the reflected light. In the area where the surface plasmon resonance wave occurs, since the incident light source is absorbed by electrons on the surface of the metal film, it can be clearly seen that, on the detector 132, compared with the metal film not contacting with the droplet, the status of the light reflected by the metal film (the detection area) contacting with the droplet is changed. The status change involves light intensity, phase, resonant wavelength and so on. The resonant conditions of the electromagnetic field will be influenced by the surrounding environment and the surface conditions. For example, when a specific biological antibody layer is grown on the metal film, the surface refractive index of the metal film grown with the specific biological antibody layer is different from that of the metal film without the specific biological antibody layer, and the combination of the biological antibody and the antigen of the sample solution may further change the surface refractive index of the metal film grown with the specific biological antibody layer. The method may also be used to observe and determine a hybridization reaction of DNA, protein, and others, and even determine combination, disassociation, and balance of chemical substances, thereby performing various biochemical detections.

Furthermore, as shown in FIG. 4, in order to reduce evapotranspiration of droplet 108 under such an architecture and prevent the droplet 108 from remaining on the fluid driving chip, an oil layer 134 (such as mineral oil) may be wrapped on the droplet 108 when the droplet 108 reaches the detection area, such that the droplet 108 is controlled in an environment fall of oil, thereby obtaining a more smooth control. The SPR detecting apparatus provided by the present invention may be used to detect 1 microlitre of droplet, and may also be used to detect a droplet less than 0.5 microlitres.

The SPR detecting apparatus provided by the present invention has been described above, and then the SPR detecting method provided by the present invention will also be described.

Firstly, an SPR detecting apparatus is provided, which may be, for example, the apparatus shown in FIG. 1. Then, a droplet is supplied to the space between the metal film and the insulation layer, and a relative voltage is provided between the first electrode and the second electrode, so as to generate a driving force to drive the droplet to the detection area where the droplet may be detected by the detector. The droplets may be continuously supplied to the space between the metal film and the insulation layer, so as to pass through the detection area sequentially. Then, the light from the light source is incident on the detection area, and in the detection area, the metal film contacts with the droplets to generate a surface plasmon resonance wave and generate a reflected light. Subsequently, the detector is used to detect the status of the reflected light. Whether the metal film contacts with the droplets will influence the status of the reflected light, and the droplets may be analyzed accordingly. The status of the reflected light involves light intensity, phase, resonant wavelength, and etc.

In the SPR detecting method, several electrodes are arranged in the flow space of the fluid and may be electrified to change the angle of the liquid and the contact surface. The electrodes may be turned on and turned off sequentially so as to control the movement of the droplets. An optical device may be used to detect the SPR phenomenon to determine the interaction between the sample droplets and the detection chip.

In the SPR detecting method, if a specific biological antibody layer is grown on the metal film, the surface refractive index of the metal film grown with the specific biological antibody layer is different from that of the metal film without the specific biological antibody layer, and the combination of the biological antibody and the antigen of the sample solution may further change the surface refractive index of the metal film grown with the specific biological antibody layer. The method may also be used to observe and determine a hybridization reaction of DNA, protein, and others, and even determine combination, disassociation, and balance of chemical substances, thereby performing various biochemical detections.

In view of the above, regarding the SPR detecting apparatus and the method thereof provided by the present invention, since the films made of a hydrophobic material are coated on the fluid driving chip and/or the detection chip, the friction force between the droplets and the fluid driving chip and/or the detection chip may be reduced, thereby controlling the droplets conveniently.

The SPR detecting apparatus and the method thereof provided by the present invention may accurately control the sequence of transferring and mixing the fluids, change the traveling path and setting upon requirements, and entirely solve the problems such as the detection chip and the sample are cross-infected, a pipeline of a micro-channel is blocked, the channel has residual, and the sample solution is wasted.

In another aspect, the SPR detecting apparatus and the method thereof provided by the present invention use the electrowetting method to control fluids, so an external pressure difference or an external pump as a driving source is unnecessary, thereby simplifying the system architecture, reducing the volume of the system, and accurately controlling the amount of the transferred liquid, even below 0.1 microliters.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A surface plasmon resonance (SPR) detecting apparatus, comprising:
    a detection chip, having a metal film, wherein the metal film has an SPR characteristic and at least one detection area; and
    a fluid driving chip, having a droplet control device, wherein the droplet control device comprises at least one first electrode and at least one second electrode, and the first electrodes are separated from the second electrodes; wherein a space for a droplet to pass through is formed between the metal film and the fluid driving chip, and a relative voltage is provided between the first electrodes and the second electrodes, so as to drive the droplet in the space.

2. The SPR detecting apparatus as claimed in claim 1, wherein the fluid driving chip further comprises:
    a substrate; and
    an insulation layer, disposed on the substrate, wherein the first electrodes and the second electrodes are disposed at different positions in the insulation layer.

3. The SPR detecting apparatus as claimed in claim 2, wherein the detection chip further comprises a first hydrophobic layer disposed on the metal film and between the metal film and the insulation layer.

4. The SPR detecting apparatus as claimed in claim 3, wherein the first hydrophobic layer has at least one opening exposing the detection area of the metal film.

5. The SPR detecting apparatus as claimed in claim 2, wherein the fluid driving chip further comprises:
    a second hydrophobic layer, disposed on the insulation layer and between the metal film and the insulation layer.

6. The SPR detecting apparatus as claimed in claim 2, wherein the detection chip further comprises a first hydrophobic layer disposed on the metal film and between the metal film and the insulation layer; and
    the fluid driving chip further comprises a second hydrophobic layer disposed on the insulation layer and between the first hydrophobic layer and the insulation layer.

7. The SPR detecting apparatus as claimed in claim 2, wherein the first electrodes and the second electrodes abut against the substrate.

8. The SPR detecting apparatus as claimed in claim 2, wherein the first electrodes abut against a lower surface of the insulation layer; and the second electrodes abut against an upper surface of the insulation layer.

9. The SPR detecting apparatus as claimed in claim 8, wherein orthographic projection planes of the first electrodes and the second electrodes do not overlap with each other.

10. The SPR detecting apparatus as claimed in claim 1, wherein the material of the metal film comprises at least one of gold, silver, copper, titanium, chromium and the mixture thereof.

11. The SPR detecting apparatus as claimed in claim 1, wherein the first electrodes and the second electrodes are arranged and disposed in an offset manner.

12. The SPR detecting apparatus as claimed in claim 1, further comprising:
    an optical device, disposed on the detection chip, the optical device comprising:
        a light source, wherein light from the light source is incident on the metal film to generate a surface plasmon resonance wave on the metal film, and meanwhile, the light from the light source is reflected; and
        a detector, for detecting a reflected light generated by the metal film.

13. The SPR detecting apparatus as claimed in claim 12, wherein the optical device further comprises:
    a prism, disposed on the detection chip and between the light source and the detector.

14. The SPR detecting apparatus as claimed in claim 13, wherein the optical device further comprises a polarizer disposed between the light source and the prism.

15. The SPR detecting apparatus as claimed in claim 12, wherein the detection chip further has a transparent substrate disposed on the metal film, and the transparent substrate is disposed between the metal film and the optical device.

16. An SPR detecting method, comprising:
providing an SPR detecting apparatus, the SPR detecting apparatus comprising:
- a detection chip, having a metal film, wherein the metal film has an SPR characteristic and has at least one detection area;
- a fluid driving chip, having a droplet control device, wherein the droplet control device comprises a plurality of first electrodes and a plurality of second electrodes disposed at different positions in an insulation layer, and a space for a droplet to pass through is formed between the metal film and the insulation layer; and
- an optical device, disposed on the detection chip and comprising a light source and a detector;

supplying at least one droplet to the space between the metal film and the insulation layer;
providing a relative voltage between the first electrodes and the second electrodes, so as to generate a driving force to drive the droplet to the detection area;
making the light from the light source be incident on the detection area to generate a surface plasmon resonance wave on the detection area and generate a reflected light; and
detecting a status of the reflected light by using the detector.

17. The SPR detecting method as claimed in claim 16, further comprising wrapping an oil layer on the droplet.

18. The SPR detecting method as claimed in claim 16, wherein the optical device farther comprises a prism disposed between the light source and the detector and a polarizer disposed between the light source and the metal film, and the method further comprises adjusting a polarizing angle of the light from the light source to be a transverse magnetic wave by using the polarizer, making the light be incident on the prism and reflected on a surface of the metal film, and generating the surface plasmon resonance wave on the surface of the metal film at the same time.

19. The SPR detecting method as claimed in claim 16, further comprising setting a substance on the detection areas of the metal film, wherein the substance and components in the droplet are combined and disassociated, so as to change the SPR characteristic of the metal film, thereby performing a biochemical detection.

20. The SPR detecting method as claimed in claim 16, further comprising continuously providing droplets to the space between the metal film and the insulation layer, and driving the droplets to pass the detection area sequentially.

21. The SPR detecting method as claimed in claim 16, wherein the detection chip further comprises a first hydrophobic layer disposed on the metal film and between the metal film and the insulation layer.

22. The SPR detecting method as claimed in claim 21, wherein the first hydrophobic layer has a plurality of openings exposing the detection area of the metal film.

23. The SPR detecting method as claimed in claim 16, wherein the fluid driving chip further comprises a second hydrophobic layer disposed on the insulation layer and between the metal film and the insulation layer.

24. The SPR detecting method as claimed in claim 16, wherein the detection chip further comprises a first hydrophobic layer disposed on the metal film and between the metal film and the insulation layer; and
the fluid driving chip further comprises a second hydrophobic layer disposed on the insulation layer and between the metal film and the insulation layer.

25. The SPR detecting method as claimed in claim 16, wherein the detection chip further has a transparent substrate, to which the metal film is attached, and the transparent substrate is disposed between the metal film and the optical device.

* * * * *